(12) United States Patent
Schneider et al.

(10) Patent No.: US 7,511,809 B2
(45) Date of Patent: Mar. 31, 2009

(54) AIR SAMPLER MODULE FOR ENHANCING THE DETECTION CAPABILITIES OF A CHEMICAL DETECTION DEVICE OR SYSTEM

(75) Inventors: Thomas Wayne Schneider, Fairfax, VA (US); James Pendell Jones, Baltimore, MD (US); Wayne Armstrong, Placitas, NM (US); Jeromy Rezac, Albuquerque, NM (US); Ratnesar-Shumate Ashni Shanna, Lorton, VA (US); Claudia Randolph, Fairfax, VA (US); Robert Almassy, Alexandria, VA (US)

(73) Assignee: ITT Manufacturing Enterprises, Inc., Wilmington, DE (US)

( * ) Notice: Subject to any disclaimer, the term of this patent is extended or adjusted under 35 U.S.C. 154(b) by 303 days.

(21) Appl. No.: 11/481,885

(22) Filed: Jul. 7, 2006

(65) Prior Publication Data

US 2008/0007728 A1 Jan. 10, 2008

(51) Int. Cl.
  *G01J 3/44* (2006.01)
(52) U.S. Cl. .................. 356/301; 356/326; 73/23.2; 73/28.01; 73/31.07
(58) Field of Classification Search .............. 356/301; 73/23.2, 28.01, 28.05, 31.07
  See application file for complete search history.

(56) References Cited

U.S. PATENT DOCUMENTS

| | | | |
|---|---|---|---|
| 4,689,052 A | 8/1987 | Ogren et al. | |
| 5,932,818 A | 8/1999 | Novick et al. | |
| 6,694,266 B1 | 2/2004 | Jackson et al. | |
| 6,732,569 B2 * | 5/2004 | Ondov et al. | 73/28.05 |
| 6,765,668 B2 | 7/2004 | Gardner, Jr. et al. | |
| 6,788,407 B1 | 9/2004 | Higdon et al. | |
| 6,847,446 B2 | 1/2005 | Shilling | |
| 6,852,527 B2 | 2/2005 | Chan et al. | |
| 6,865,196 B2 | 3/2005 | Dobbs et al. | |
| 6,865,926 B2 | 3/2005 | O'Brien et al. | |
| 6,893,876 B2 | 5/2005 | Perraut et al. | |
| 6,917,423 B2 | 7/2005 | Gardner, Jr. et al. | |
| 6,949,734 B2 | 9/2005 | Neff et al. | |
| 6,952,945 B2 | 10/2005 | O'Brien | |
| 6,985,818 B1 | 1/2006 | Samuels | |
| 7,009,170 B2 | 3/2006 | Dobbs et al. | |
| 7,012,249 B2 | 3/2006 | Krutchinsky et al. | |

(Continued)

OTHER PUBLICATIONS

S. Hong, J. Birmingham, M. Fountain, "Mesochannel Gas Sampler for Rapid Sample Collection and Concentration," Mar. 2001, pp. 1-15, Prepared for the Department of Energy Under DOE Grant No. DE-FG03-00ER83048 by MesoSystems Technology, Inc. Kennewich, Washington.

(Continued)

*Primary Examiner*—L. G Lauchman
(74) *Attorney, Agent, or Firm*—Edell, Shapiro & Finnan, LLC

(57) ABSTRACT

An air sampler module is provided for use with a detection device that monitors liquids and/or solids on a surface using spectroscopy techniques. The air sampler module comprises a housing, an intake port for collecting air containing airborne threats to be analyzed by the detection device, and a port to permit communication of an optical transceiver of the detection device into the housing to permit analysis of the collected air. Thus, the capabilities of a spectroscopy detection system are expanded to include the ability to analyze airborne threats.

22 Claims, 7 Drawing Sheets

U.S. PATENT DOCUMENTS

| | | |
|---|---|---|
| 7,113,275 B2 | 9/2006 | Gardner, Jr. et al. |
| 2002/0031843 A1 | 3/2002 | Harmon |
| 2003/0223063 A1 | 12/2003 | Hill et al. |
| 2004/0198927 A1 | 10/2004 | Battiste |
| 2004/0239913 A1 | 12/2004 | Kobayashi et al. |
| 2004/0248319 A1 | 12/2004 | Belyakov et al. |
| 2005/0105079 A1 | 5/2005 | Pletcher et al. |
| 2005/0179893 A1 | 8/2005 | Hill et al. |
| 2005/0214168 A1 | 9/2005 | Lin et al. |
| 2005/0280814 A1 | 12/2005 | Iuliano |
| 2006/0061762 A1 | 3/2006 | Dwight et al. |

OTHER PUBLICATIONS

Lockheed Martin Maritime Systems & Sensors, "Biological Aerosol Warning System," Cleared for Public Domain Release DoD/00-S-0607, Dec. 1999, Aug., 2003, Manassas, Va.

General Dynamics Armament and Technical Products, "Biological Agent Warning Sensor," 2007, Charlotte, NC.

* cited by examiner

AIR SAMPLER MODULE FOR ENHANCING THE DETECTION CAPABILITIES OF A CHEMICAL DETECTION DEVICE OR SYSTEM

BACKGROUND OF THE INVENTION

The present invention relates to spectroscopy detection devices and systems.

Spectroscopy techniques are used to analyze substances and techniques have been developed to remotely monitor surfaces on which harmful substances in solid and liquid phases may be present. Detection systems are known that use other technologies, such as gas chromatography, to detect harmful substances in the gas/vapor phase.

There are, however, no Raman systems are known that address the detection of aerosolized particles and vapor.

SUMMARY OF THE INVENTION

Briefly, according to one aspect of the invention, an air sampler module is provided for use with a detection device that monitors liquids and/or solids on a surface using spectroscopy techniques. The air sampler module comprises a housing, an intake port for collecting air to be analyzed by the detection device, a virtual impactor in the housing that sorts particles in the air collected through the intake port to produce a first flow primarily containing aerosol particles to be analyzed and a second flow primarily containing vapor to be analyzed and a port to permit communication of an optical transceiver of the detection device into the housing to permit analysis of particles the first and second flows. Thus, the combination or integration of the optical detection device with the air sampler module provides a spectroscopy detection system that has the capability of analyzing solid or liquid substances that have been deposited on a surface (external to the air sampler module), such as on a road, wall or other ground surface, and to analyze airborne aerosolized particles as well as vapors that the air sampler module collects.

According to another aspect of the invention, a method and a combination is provided for analyzing airborne and non-airborne threats using spectroscopy techniques in which air to be analyzed is collected in a housing. The airborne aerosol particles are deposited onto at least a first surface in the housing. An optical transceiver of a detection device is optically coupled to the surface inside the housing to permit spectroscopy analysis of the particles deposited on the first surface inside the housing. In addition, the optical transceiver is optically coupled to a surface outside the housing to permit spectroscopy analysis of particles on the surface outside of the housing.

DETAILED DESCRIPTION

Raman spectroscopy is very versatile and can detect and identify most chemicals, providing the amount of chemical present is sufficient to generate signal strengths that meet the minimum signal-to-noise ratio (SNR) requirements of the spectroscopy system. Due to the low concentration of target molecules, aerosols must be concentrated before detection is possible. According to an embodiment of the invention, an air sampler module is provided that can augment the functions of an existing spectroscopy system or that may be integrated into such a system to expand its functions to include airborne particles in addition to pre-existing capabilities of the system to analyze solids and liquids already deposited on a surface.

Figure 1:
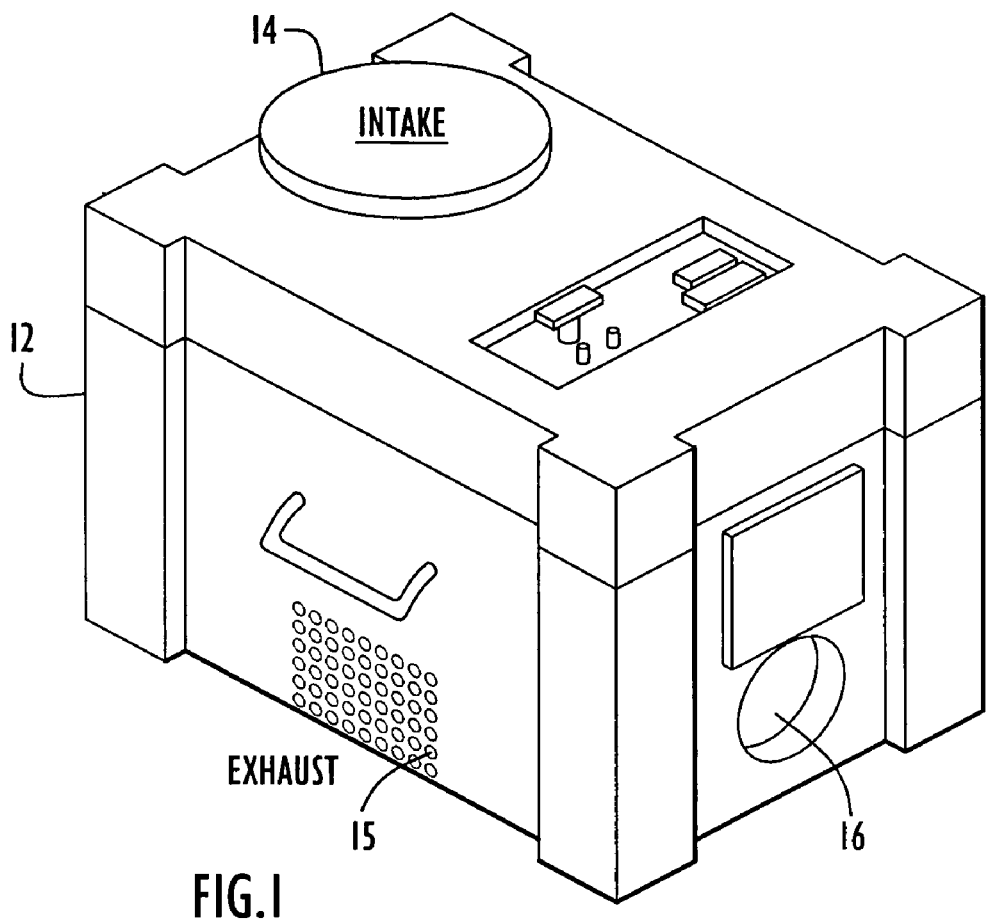
FIG. 1 is a perspective view of an air sampler module according to an embodiment of the invention.
Figure 2:
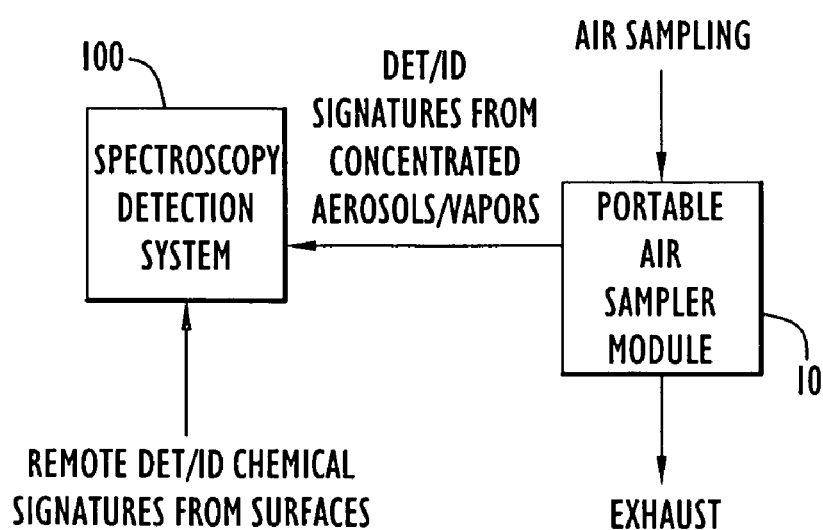
FIG. 2 is a block diagram showing how the air sampler module interfaces with a detection device or system.

Referring first to FIGS. 1 and 2, the air sampler module is generally shown at reference numeral 10 and comprises a housing 12 having an intake port 14, an exhaust port 15 and an optical interrogation port 16. The exhaust port 15 exhaust air collected in the housing 12 after it has been analyzed. The air sampler module 10 is designed to be integrated into an existing spectroscopy detection device or system, such as a Raman system, as shown in FIG. 2 shown at 100. The function of the air sampler module 10 is to capture aerosolized particles as well as vapors so that they can be interrogated by the spectroscopy detection system 100. The detection system 100 may be one that is already capable of remotely analyzing surfaces for various substances. Thus, by integrating or interfacing the air sampler module 10 to the detection system 100, the capabilities of the detection system 100 are expanded to monitor for substances in all three phases of matter (solids, liquids and gas or vapor). For example, and without limitation, the detection system 100 capabilities may be expanded to detect for any non-traditional agents (NTAs), toxic industrial chemicals (TICs) and chemical or biological warfare agents (CWAs) in all phases of matter.

One advantage of the air sampler module 10 is that it does not require a new detection technique; it can be used with a proven detection system 100 that is already in use for detecting chemicals on surfaces, thereby leveraging the same system to detect aerosols and vapors. Consequently, it is possible to search/scan for aerosols before liquid is on the ground, and for vapors when no liquid will be detected on the ground. In addition, it makes it possible to search/scan for aerosols, vapors, and solid/liquid chemicals on the ground independent of each other, or in combination(s). An example of a detection system 100 is the LISA™ Raman detector manufactured and marketed by ITT Industries. The LISA™ Raman detector is capable of performing standoff or remote surface detection of solids and liquids.

The benefits of integrating the air sampler module 10 into an existing and known detection technology in conjunction with the air sampler module 10 are numerous. The distinctive "spectral fingerprints" from the different vibrational modes that are characteristic of each type of molecule are already known and an existing library of CWAs and TICs may be used for the collected air samples. The ability to use an ultraviolet (UV) Raman light source minimizes interference due to background fluorescence and elimination of daylight interference due to solar blind operation. In addition, a UV Raman resonance achieves enhancement of specific spectral features, and quadratic increase in Raman cross-section with decreasing wavelength. Remote or near-standoff sensing may be achieved by directly interrogating the liquid and/or solid phase chemicals on the contaminated surface (without surface contact and sample preparation or concentration). The term "standoff" in this context is meant to define a distance range of approximately a few centimeters to meters. Thus, the detection system 100 has a Raman light source and a detector that detects Raman scattered light from a sample surface. A detection system 100 equipped with the air sampler module 10 has operational flexibility: it may operate in a single-shot on-the-move detection mode or in a stationary staring mode.

Figure 3:
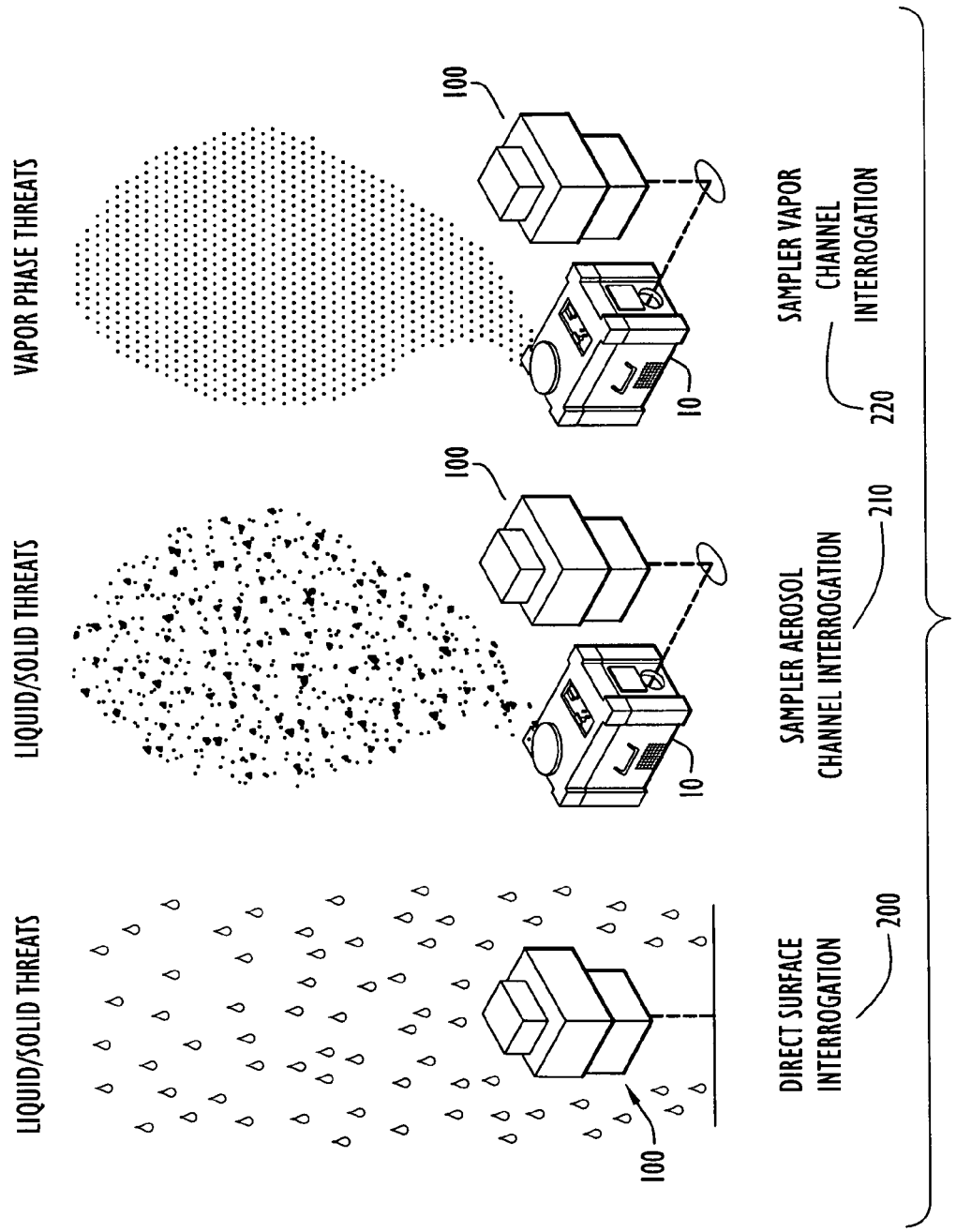
FIG. 3 is a diagram depicting the capabilities provided by the air sampler module to an existing detection device or system.

Turning to FIG. 3, the capabilities of a detection system 100 afforded by integration of the air sampler module 10 are shown. The air sampler module 10 provides for the capability to monitor airborne threats that are in a solid, liquid or vapor form. The airborne threats are either an aerosol or vapor. For example, aerosol threats are airborne particles in liquid or solid form that are in the range of 1-100 microns in size whereas vapor threats are molecules (substantially smaller than 1 micron) distributed in the localized air mass, where the localized air acts as a solvent. Vapor threats represent a class of threat that does not exist in the particle state. A detection system 100 equipped with the air sampler module can monitor for liquid/solid threats that have already fallen onto a surface outside of the air sampler module 10 using direct surface interrogation as shown at 200, for smaller liquid/solid particle threats by interrogating an aerosol channel of the air sampler module 10 as shown at 210, and for vapor phase threats by interrogating a vapor channel of the air sampler module 10 as shown at 220. As such, the detection system 100 can monitor for airborne threats (aerosol and/or vapor) only, airborne threats in tandem with non-airborne threats already deposited (e.g., fallen or otherwise deposited) on surfaces outside of the air sampler module or non-airborne threats only that are deposited on surfaces outside of the air sampler module.

Figure 4:
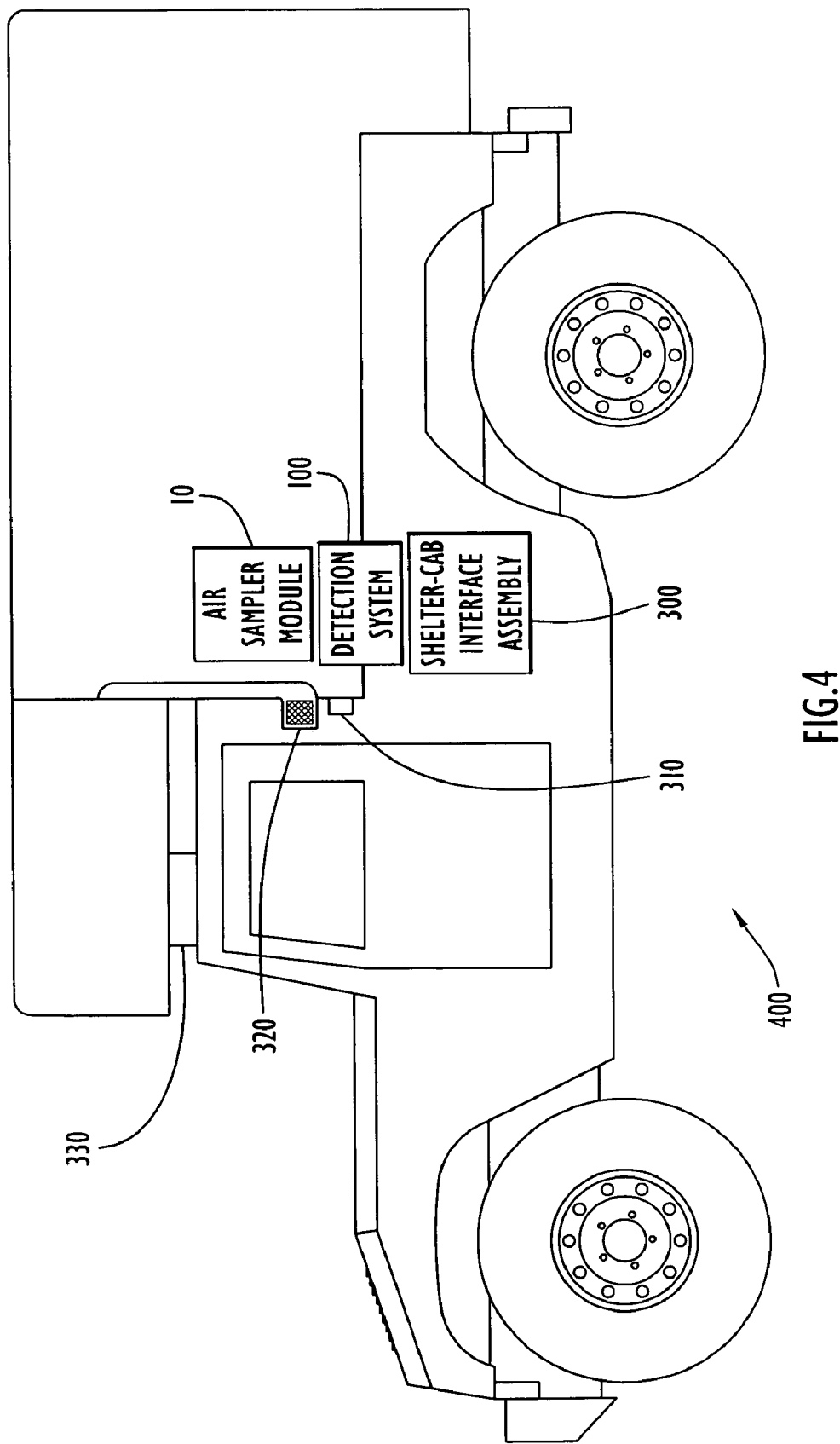
FIG. 4 is a schematic diagram depicting use of the air sampler module with a vehicle-mounted detection device or system.

The air sampler module 10 may be integrated into a detection system 100 in a variety of deployment platforms. FIG. 4 illustrates a moving vehicle deployment platform according to an embodiment of the invention where the detection system 100 integrated with the air sampler module 10 is mounted inside a contaminent protection shelter on the vehicle 400. A shelter-cab interface assembly 300 is provided that performs two functions: 1) isolates and preserves the integrity of the vehicle shelter, and 2) optically couples the detection system to the air sampler module and the ground, a function that is described hereinafter in connection with FIG. 6. There is an input/output box 310 that holds a movable directional air intake vent 320 and an air return bellows 330. The movable directional air vent 320 is coupled to the intake port of the air sampler module and is used to capture air that is to be analyzed. The air return bellows 330 exhausts the air from the air sampler module 10 to the atmosphere in such a manner as to avoid introducing the exhausted air back into the intake vent 320. A vehicle 400 equipped with a detection system 100 and a continuous operating air sampler module 10 provides for the capability of detecting surface contamination (liquid and/or solid) by scanning a surface beneath the vehicle 400 and airborne contamination in an environment at relatively high travel speeds.

Raman spectroscopy is very versatile and can detect and identify most chemicals, providing the amount of chemical present is sufficient to generate signal strengths that meet the minimum signal-to-noise ratio (SNR) requirements of the system.

Figure 5:
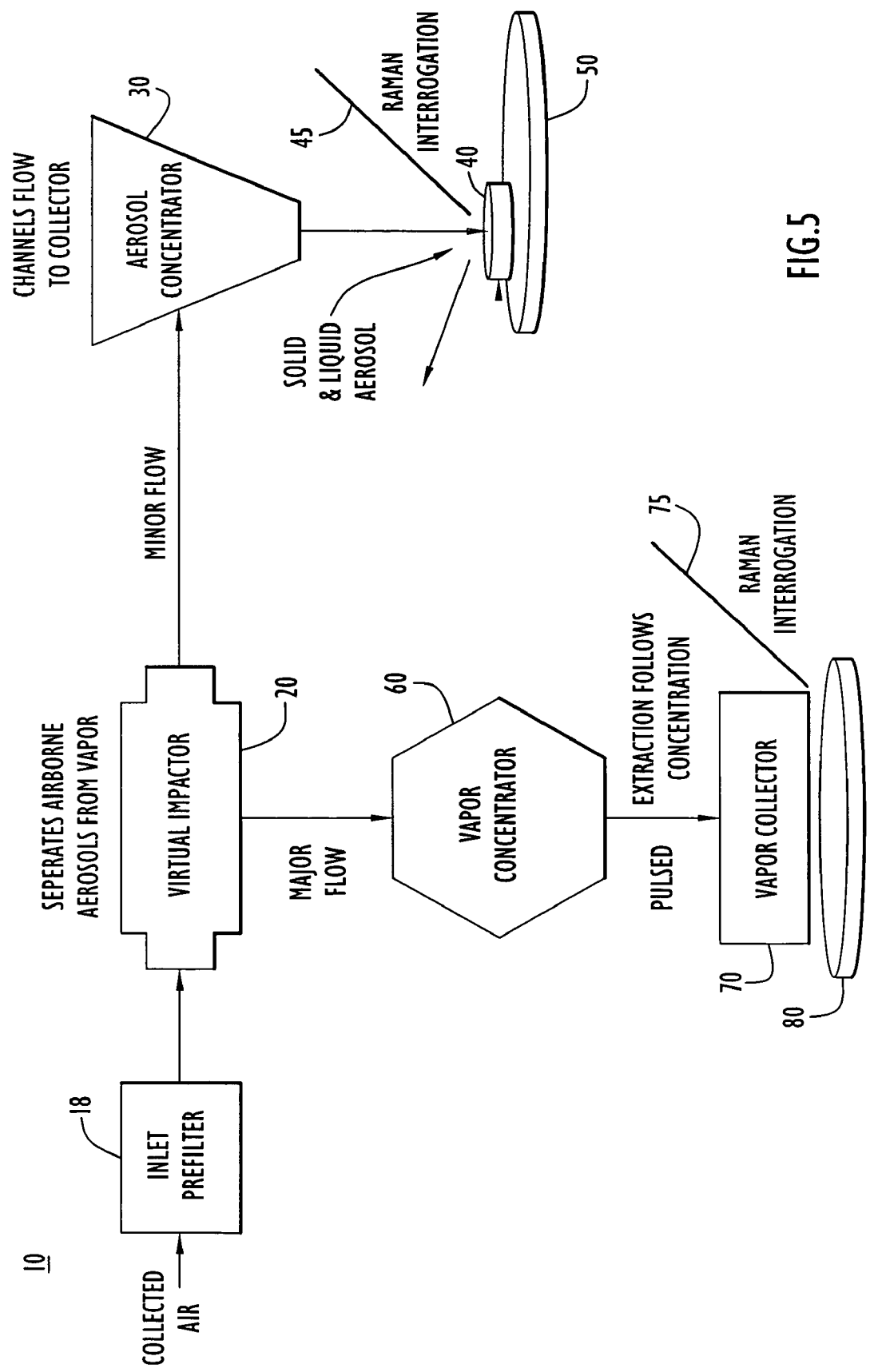
FIG. 5 is a schematic diagram showing how the air sampler module provides optical access to an optical transceiver in a detection device or system according to an embodiment.

Turning to FIG. 5, a block diagram illustrating components of the air sampler module 10 is provided according to one embodiment. The air sampler module comprises an inlet prefilter 18 that filters collected air and supplies the filtered air to a virtual impactor 20. The virtual impactor 20 has two output paths. The first output path or flow is an aerosol path where air flow is directed to an aerosol concentrator 30 after processing by the virtual impactor. The output of the aerosol concentrator 30 is directed to an aerosol collector 40 on a carousel staging mechanism 50. The second output path or flow from the virtual impactor 20 is a vapor path where air flow is directed to a vapor concentrator 60. The vapor concentrator 60 outputs vapor to a vapor collector 70 on a carousel staging mechanism 80.

Air is collected at an accelerated rate, for example, 40 L/min in one embodiment, which enables separation of aerosols from vapors using the virtual impactor 20. The aerosol path from the virtual impactor 20 to the aerosol concentrator is also referred to as the "minor flow" because the majority of the accelerated aerosol mass is concentrated, via inertia, into a smaller volume of air. The vapor path from the virtual impactor 20 to the vapor concentrator 60 is referred to as the "major flow" because it contains the majority of the sampled air flow. Vapors are separated from larger particles due to the lack of inertia. These two outputs create two channels within the air sampling module: aerosol and vapor. Raman detection or analysis of aerosols and vapors are independent measurements made by the host detection system as shown in FIG. 5, but made through the same optical port of the air sampler module 10. Moreover, although these two measurements are independent, they are accomplished automatically with one setup using coupling optics described hereinafter in connection with FIG. 6.

The inlet prefilter 18 is a mechanical device that acts like a self cleaning filter to prevent larger particles from entering the virtual impactor 20 and clogging the aerosol and vapor paths. For example, in one embodiment, the inlet prefilter 18 comprises a large mesh input screen to keep bugs and other debris out and following this screen is an aerodynamic tube assembly that acts on the principle of inertial impaction and separates and discards particles greater than a certain size, e.g., 100 μm. The main flow is then channeled into the virtual impactor 20.

The virtual impactor 20 is a device for concentrating and size sorting airborne particles without impacting them on a surface. It uses a combination of nozzles to separate particles above a particle diameter "cut size" from the rest of the particles in the aerosol cloud. The virtual impactor 20 splits the inlet flow into the major flow and the minor flow. In one embodiment, the major flow represents about 90% of the inlet air and about 90% of the particles smaller than the cut size and the minor flow represents the remaining percentage of the inlet air but contains most (typically 70-90%) of the particles that are greater than the cut size. For example, if the cut size is 1 micron, then the minor flow would contain 7-9 times higher concentration of particles in the 1-10 micron size range relative to the inlet air. Not by way of limitation, an example of a commercially available virtual impactor that may be used in the air sampler module 10 is a MicroVIC® Particle Concentrator, manufactured by MesoSystems Technology, Inc.

The aerosol path or channel from the virtual impactor 20 has two operating states or modes: (a) impaction of the aerosol, followed by (b) detection. The aerosol concentrator 30 directs the aerosol particles (solid or liquid) through an impaction nozzle and to the aerosol collection surface 40. The Micro VIC® is equipped with these nozzles. The aerosol collection surface 40 is, for example, a disk or a plate shaped device. The aerosol cloud is accelerated through the aerosol concentrator 30 and directed at the aerosol collector 40. The aerosol particles, due to their inertia, impact directly on the aerosol collector 40. The efficiency of capture is dependent on both the design of the aerosol concentrator 30 and the aerosol collector substrate 40 onto which the particles are impacted.

The spot diameter deposited on the surface may be, in one embodiment, approximately 2 mm in diameter or otherwise a size for which the detector system optics can focus and interrogate. For example, an aluminized surface may be used as the aerosol collection substrate 40. Current designs of aerosol collectors rely on passive surface tension and some residual electrostatic attraction to hold the aerosol solid or liquid particles onto the collector. Examples of other suitable materials for the aerosol collector 40 are ultrafine filters fabricated from paper, metals, or plastic.

The carousel staging mechanism 50 is a staging point for aerosol collection surfaces 40 in order to sequentially deposit the aerosols onto a new, clean surface.

Solid and liquid aerosol particles are captured on the aerosol collector 40 and are interrogated by the host detection system as shown by the interrogation beam 45 and described hereinafter in connection with FIG. 6.

The vapor path or channel from the virtual impactor 20, unlike the aerosol channel has three operating states or modes: (a) concentration of the vapor, (b) desorption of the concentrated vapor, followed by (c) detection. Detection is made after the vapor is desorbed from the concentrator into the vapor collector 70 that accommodates the spectroscopy interrogation beam 75. In operation, the detection system may tag the data, such as Raman data, to indicate the source of the sample (external surface via the detection system's existing capability, vapor or aerosol).

While the figures show a single interrogation port 16, it should be understood that an alternative is to have two or more interrogation ports. For example, there may be an interrogation port dedicated to the aerosol channel and an interrogation port dedicated to the vapor channel. Thus, in general, the air sampler module 10 has at least one interrogation port.

Figure 6:
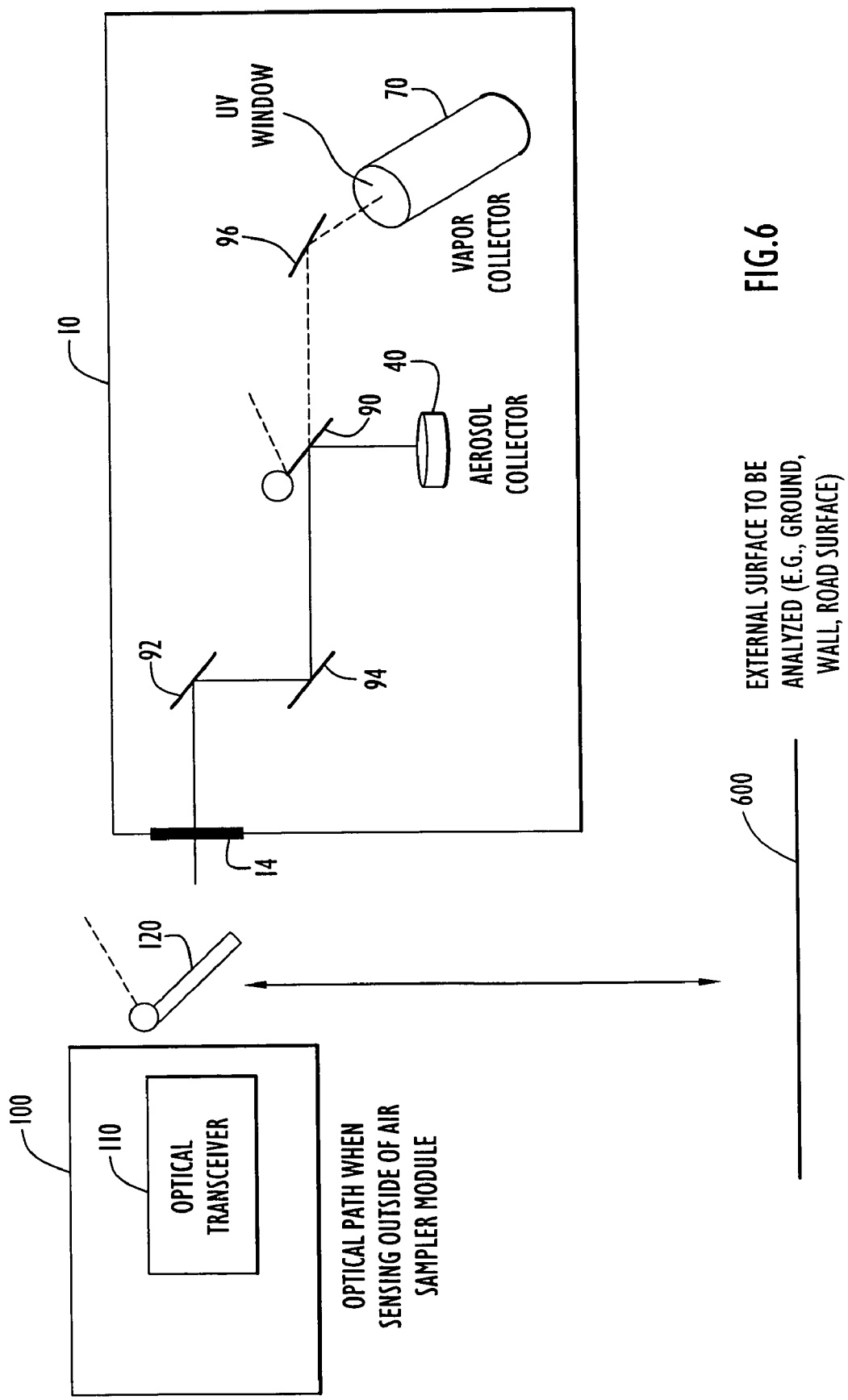
FIG. 6 is a block diagram showing a possible detector optical path to two the aerosol collector and the vapor collector of the air sampler module, combined with an optical path for analysis of a surface external to the air sampler module, according to an embodiment.

Turning to FIG. 6, the optical paths to the aerosol collector 40 and the vapor collector 70 of the air sampler module 10 are described in more detail according to one embodiment. Reference numeral 110 is an optical transceiver component of the detection system 100 (FIGS. 1 and 2). The optical transceiver component 110 transmits an interrogating beam of light, such as from a Raman laser light source, and then receives scattered light from the sample. The air sampler module 10 comprises a network of optical elements to direct the interrogating light beam to both the aerosol collector 40 and the vapor collector 70. In one embodiment, there is a flipper mirror 90 that is movable between first and second positions. In a first position, the mirror 90 directs the interrogation light from the optical transceiver 110 to the aerosol collector 40 and then reflects back the scattered light from the sample on the aerosol collector 40 to the optical transceiver 110. In a second position, the mirror is moved out of the optical path between the vapor collector 70 and the optical transceiver 110. This second position is shown by the dotted lines in FIG. 6. There are several optional turning mirrors 92, 94 and 96 that may be provided in order to direct the light to and from the optical transceiver around the required bends in the optical paths to allow for reducing the size of the air sampler module 10. When mirror 90 is in the second position, light from the optical transceiver 110 is reflected by mirrors 92, 94 and 96 to the vapor collector 70, and in the reverse direction light scattered from the sample on the vapor collector is reflected by mirrors 96, 94 and 92 back to the optical transceiver 110.

In addition, with continued reference to FIG. 6, there is an optical element 120 that can be adjusted or actuated to change the optical path for the optical transceiver 110 to either the air sampler module 10 or to a surface 600 external to the air sampler module 10, such as a road surface, ground/floor, wall, etc. In one embodiment, the optical element 120 may be a turning mirror that is adjusted between first and second positions, where in a first position the optical transceiver 110 has an optical path with the air sampler module 10 and in a second position the optical transceiver has an optical path with the external surface 600. A user interface control is provided to allow a user to select either operation mode (air sampler module or external surface) and the optical element 120 would be adjusted in response to the user's selection. Alternatively, the optical element 120 may be a beam splitter device. The optical element 120 may be included as part of the detection system 100, the air sampler module 10, or a component separate from both the detection system 100 and air sampler module 10. While FIG. 6 shows that the optical element 120 is interrupting physical path between the air sampler module 10 and the optical transceiver 110 when forming the optical path with the external surface 600, it should be understood that the system may be designed such that optical element 120 may be positioned and configured to be positioned to interrupt the physical path when creating the optical path to the air sampler module 10 instead and moved out of the physical path of the optical transceiver 110 when analyzing the external surface 600.

Many technologies are known for performing the function of the vapor concentrator 60. Two examples of suitable devices are the "Mesochannel" gas sampler (MGS) concentrator, developed by MesoSystems Technologies, Inc., with U.S. government support; and a version of the Cascade Avalanche Sorbent Plate Array (CASPAR) concentrator developed at the U.S. Naval Research Laboratory, but commercially available.

Figure 7:
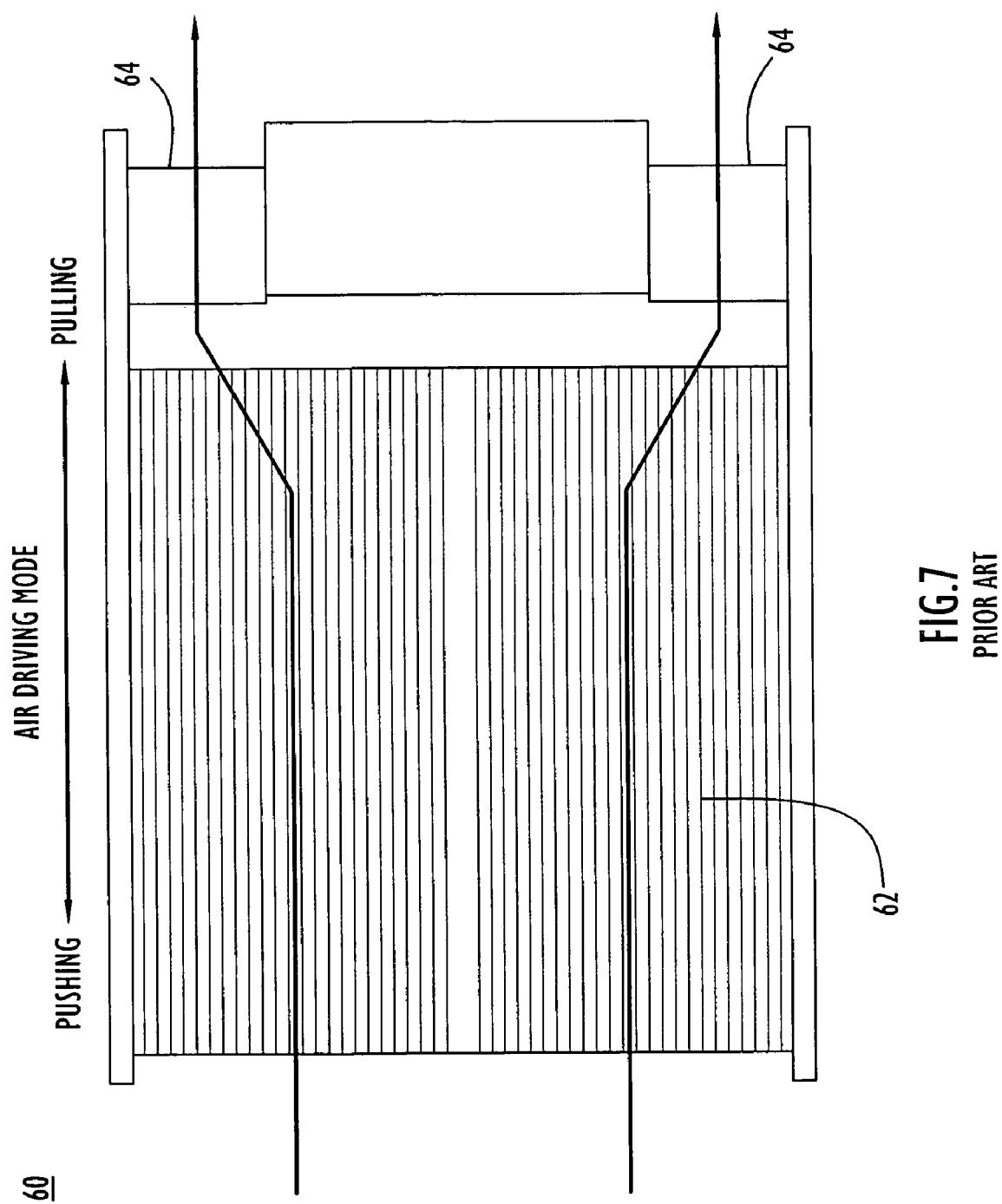
FIG. 7 is a perspective view of one type of known vapor concentrator useful in the air sampler module according to one embodiment.

FIG. 7 illustrates a cross-sectional view of the MGS as an example of a vapor concentrator 60. The MGS is composed of small channels 62 coated with adsorbent. The MGS has an adsorbent core design and therefore simple low power fans 64 may be used to push the flow through them. The walls of the channels 62 can be heated electrically to rapidly desorb any collected contaminants so that the vapor collection channel can be reused. The heat drives off the concentrated vapor and then the collector is moved back into the carousel and reused for a subsequent/following collection. During a relatively high-flow-rate loading phase, gas-phase contaminants are adsorbed onto the channel walls. After less than one minute of loading, the channel walls are rapidly heated in order to desorb the collected contaminants and deliver them to the vapor collector 70 for detection.

Microfabrication of thermally isolated and low heat capacity structures has been known to provide advantages in terms of rapid heating at very low power. This has been used for microhotplate sensors that can operate at hundreds of degrees above ambient on tens to hundreds of mW of power. Researchers at the Naval Research Laboratory have recently demonstrated a microfabricated preconcentrator design that takes advantage of these thermal characteristics along with a flow design that enables high volume sampling with low pressure drops (key for minimizing sampling pump size and power requirements).

Figure 8:
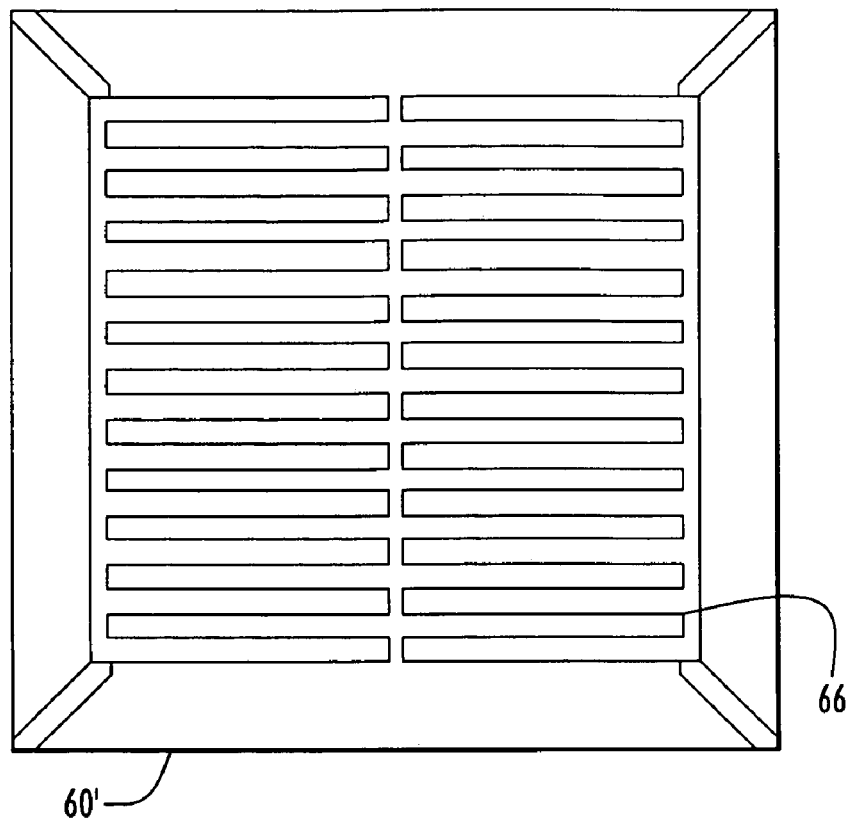
FIGS. 8 and 9 are enlarged views of another type of known vapor concentrator useful in the air sampler module according to one embodiment.
Figure 9:
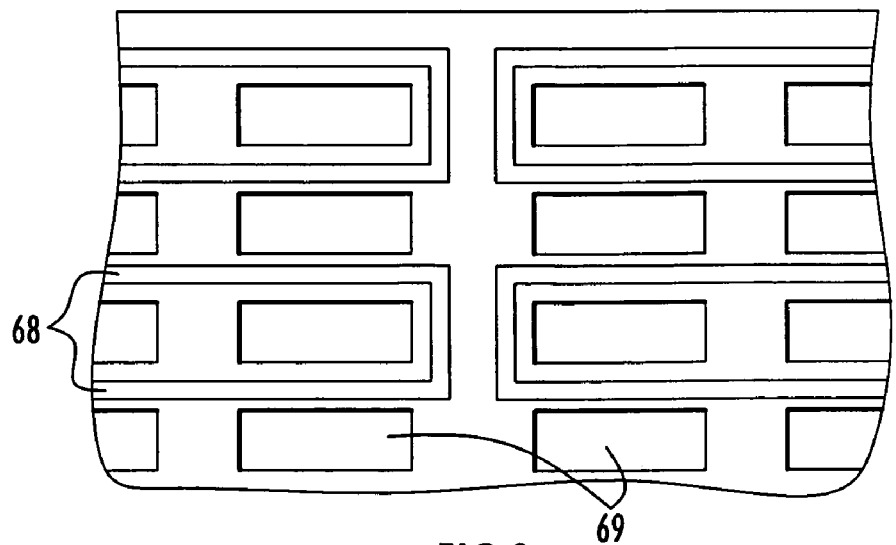

FIGS. 8 and 9 illustrate the CASPAR preconcentrator as another example of a vapor concentrator that may be used in the air sampler module 10 according to one embodiment. The CASPAR device, shown at reference numeral 60' comprises a thin membrane 66 attached to a silicon substrate through narrow tethers 68 formed using a low stress silicon nitride layer that is selectively etched. This thermal isolation enhances the ability to rapidly heat the membrane with low power. To provide the low flow resistance, a series of holes 69 are formed in the membrane and the air flow is allowed to flow vertically through the membrane. The small dimensions of the holes 69 provide enhanced diffusional capture of analytes on an adsorbent layer that is deposited on the membrane.

A meander line heater around the holes is used to rapidly heat the membrane for thermal desorption. Advantages of the CASPAR concentrator technology over more typical adsorbent bed preconcentrators include, without limitation, high volumetric flow rate (tens of L/min), low power heating (hundreds of mW), and rapid thermal desorption (msec thermal rise times).

Vapor concentration by either an MGS type device (FIG. 7) or a CASPAR type device (FIGS. 8 and 9) is allowed to continue until the minimum amount of air is processed through the device to build the concentration level, as dictated by a complete chemical signature analysis of the designated list of chemicals of interest. After a vapor has been concentrated, the adsorbed molecules are desorbed on the vapor collector 70.

There are several methods of collecting the concentrated vapor for Raman interrogation, including without limitation, a cold plate, a micro porous surface or a vacuum cell.

A cold plate design is based on the principle that if a vapor impinges on a cold surface, the vapor condenses to yield a liquid. This liquid can then be interrogated using a Raman-based detection system as described above for collected aerosol particles. In one embodiment, cooling the cold plate may be done with an integral thermal electric cooler (TEC). Collecting water vapor can be minimized using dry air in the desorption step of the vapor concentrator. The cold plate may be cleaned by applying heat to it to drive off the liquid.

The system and methods described herein may be embodied in other specific forms without departing from the spirit or essential characteristics thereof. The foregoing embodiments are therefore to be considered in all respects illustrative and not meant to be limiting.

What is claimed is:

1. An air sampler module for use with a detection device that monitors liquids and/or solids on a surface using spectroscopy techniques, the detection device comprising an optical transceiver, the air sampler module comprising a housing, an intake port for collecting air to be analyzed, a virtual impactor in said housing that sorts the air collected to produce a first flow primarily containing aerosol particles to be analyzed and a second flow primarily containing vapor to be analyzed and a port to permit communication of the optical transceiver of the detection device into said housing to permit analysis of said first and second flows.

2. The air sampler module of claim 1, and further comprising an aerosol concentrator coupled to the first flow that deposits solid and/or liquid aerosol particles onto a first surface for spectroscopy analysis with the use of the optical transceiver of the detection device.

3. The air sampler module of claim 2, and further comprising a vapor concentrator coupled to the second flow that concentrates vapor onto a second surface for spectroscopy analysis with the use of the optical transceiver of the detection device.

4. The air sampler module of claim 3, wherein the vapor collector comprises heating elements that heat the vapor in order to drive off concentrated vapor to allow for reuse of the second surface for a new sample.

5. The air sampler module of claim 3, wherein said second surface is cooled so that vapor condenses to produce liquid on it.

6. The air sampler module of claim 3, and further comprising at least one optical element in said housing that provides a first optical path between said optical transceiver to said first surface and a second optical path between said optical transceiver and said second surface.

7. The air sampler module of claim 6, wherein said at least one optical element is a mirror that is movable between a first position to create the first optical path and a second position to create the second optical path.

8. In combination, the air sampler module of claim 1, and a Raman detection device comprising the optical transceiver, wherein the optical transceiver is capable of being directed to a surface outside of said air sampler module to perform near-standoff or remote detection.

9. A spectroscopy detection system comprising:
   an optical transceiver that emits a beam of light onto a surface and detects scattered light from the surface for spectroscopy analysis of substances on the surface; and
   an air sampler module comprising a housing, an intake port for collecting air to be analyzed; a virtual impactor in said housing that the air collected through the intake port to produce a first flow primarily containing aerosolized particles to be analyzed and a second flow primarily containing vapor to be analyzed and at least one port to permit communication of the optical transceiver into said housing to permit spectroscopy analysis of said first and second flows.

10. The system of claim 9, and further comprising at least one optical element that is capable of providing an optical path between said optical transceiver to a surface outside of said air sampler module to perform near-standoff or remote detection on the surface outside the air sampler module.

11. The system of claim 9, and wherein the air sampler module further comprises an aerosol concentrator coupled to the first flow that deposits solid and/or liquid aerosol particles onto a first surface for spectroscopy analysis with the use of the optical transceiver.

12. The system of claim 11, and further comprising a vapor concentrator coupled to the second flow that concentrates vapor from the second flow on a second surface for spectroscopy analysis with the use of the optical transceiver.

13. The system of claim 12, and further comprising at least one optical element in said housing that provides a first optical path between said optical transceiver to said first surface and a second optical path between said optical transceiver and said second surface.

14. The system of claim 9, wherein said optical transceiver emits an interrogation light beam and detects Raman scattered light.

15. The system of claim 9, wherein the air sampler module further comprises an exhaust port to exhaust air collected in the housing into the atmosphere after it has been analyzed.

16. A method for analyzing airborne and non-airborne threats using spectroscopy techniques, the method comprising:
   collecting in a housing air to be analyzed;

sorting the air collected in the housing into a first flow containing aerosolized liquid and/or solid particles and a second flow containing vapor;

depositing the aerosolized liquid and/or solid particles onto a first surface in the housing and the vapor onto a second surface in the housing; and optically coupling the optical transceiver to at least one of said first and second surfaces in the housing to permit spectroscopy analysis of said liquid and/or solid aerosol particles or of said vapor.

17. The method of claim 16, wherein and further comprising heating said vapor from the second flow and condensing liquid from the vapor onto said second surface.

18. The method of claim 16, wherein when analyzing aerosolized particles, said optically coupling comprises directing a beam of light from said optical transceiver to said first surface and directing scattered light from said first surface to said optical transceiver, and when analyzing vapor, said optically coupling comprises directing the beam of light from said optical transceiver to said second surface and directing scattered light from said second surface to said optical transceiver.

19. The method of claim 16, and further comprising creating an optical path between said optical transceiver and a surface outside of said housing to perform near-standoff or remote detection of solid and/or liquid substances on the surface outside of said housing.

20. A method for analyzing airborne and non-airborne threats using spectroscopy techniques, the method comprising:

collecting in a housing air to be analyzed;

depositing the airborne particles onto at least one surface inside said housing;

optically coupling the optical transceiver to said at least a first surface in the housing to permit spectroscopy analysis of the particles deposited thereon; and optically coupling the optical transceiver to a surface outside of the housing to permit spectroscopy analysis of particles on the surface outside of the housing.

21. The method of claim 20, and further comprising directing vapor from the air collected in the housing to a second surface in said housing, and wherein optically coupling further comprises optically coupling the optical transceiver to said second surface in the housing to permit spectroscopy analysis of the vapor on said second surface.

22. In combination, a detection device comprising an optical transceiver, and an air sampler module comprising a housing, an intake port for collecting air containing to be analyzed, and at least one port to permit communication of the optical transceiver of the detection device into said housing to permit analysis of said air, and further comprising at least one optical element that is capable of providing a first optical path between said optical transceiver of the detection device and a surface outside of said air sampler module to perform near-standoff or remote detection on the surface outside of the air sampler module and providing a second optical path between the optical transceiver and said port of said air sampler module to permit analysis of threats contained in the air collected in said housing.

* * * * *

UNITED STATES PATENT AND TRADEMARK OFFICE
CERTIFICATE OF CORRECTION

| | |
|---|---|
| PATENT NO. | : 7,511,809 B2 |
| APPLICATION NO. | : 11/481885 |
| DATED | : March 31, 2009 |
| INVENTOR(S) | : Thomas Wayne Schneider et al. |

Page 1 of 1

It is certified that error appears in the above-identified patent and that said Letters Patent is hereby corrected as shown below:

Col. 8, line 30: "analyzed ;" should read "analyzed,"

Col. 8, line 31: "said housing that the air" should read "said housing that sorts the air"

Signed and Sealed this

Twenty-sixth Day of May, 2009

JOHN DOLL
*Acting Director of the United States Patent and Trademark Office*

UNITED STATES PATENT AND TRADEMARK OFFICE
CERTIFICATE OF CORRECTION

PATENT NO.       : 7,511,809 B2
APPLICATION NO.  : 11/481885
DATED            : March 31, 2009
INVENTOR(S)      : Thomas Wayne Schneider et al.

It is certified that error appears in the above-identified patent and that said Letters Patent is hereby corrected as shown below:

Column 2, line 59, replace "ITT Industries" with -- ITT Corporation --;

Column 7, line 63, replace "for spectroscopy" with -- for spectroscopic --;

Column 8, line 1, replace "for spectroscopy" with -- for spectroscopic --;

line 25, replace "for spectroscopy" with -- for spectroscopic --;

line 28, replace "for spectroscopy" with -- for spectroscopic --;

line 36, replace "for spectroscopy" with -- for spectroscopic --;

line 46, replace "for spectroscopy" with -- for spectroscopic --;

lines 50-51, replace "for spectroscopy" with -- for spectroscopic --;

line 64, replace "using spectroscopy" with -- using spectroscopic --;

Column 9, line 9, change "spectroscopy analysis" with -- spectroscopic analysis --;

Column 9, line 29, change "using spectroscopy" with -- using spectroscopic --;

UNITED STATES PATENT AND TRADEMARK OFFICE
CERTIFICATE OF CORRECTION

PATENT NO. : 7,511,809 B2
APPLICATION NO. : 11/481885
DATED : March 31, 2009
INVENTOR(S) : Thomas Wayne Schneider et al.

It is certified that error appears in the above-identified patent and that said Letters Patent is hereby corrected as shown below:

Column 10, line 5, change "permit spectroscopy" with -- permit spectroscopic --;

line 8, change "permit spectroscopy" with -- permit spectroscopic --; and line 14, change "permit spectroscopy" with -- permit spectroscopic --.

Signed and Sealed this

Seventh Day of July, 2009

JOHN DOLL
*Acting Director of the United States Patent and Trademark Office*